United States Patent
Zander et al.

(10) Patent No.: US 7,569,055 B2
(45) Date of Patent: Aug. 4, 2009

(54) OSTEOSYNTHETIC AID

(75) Inventors: Nils Zander, Eckernförde (DE); Axel Cremer, Fahrenkrog (DE); Michael Seemann, Altenholz (DE)

(73) Assignee: Stryker Trauma GmbH (DE)

( * ) Notice: Subject to any disclaimer, the term of this patent is extended or adjusted under 35 U.S.C. 154(b) by 571 days.

(21) Appl. No.: 10/735,975

(22) Filed: Dec. 15, 2003

(65) Prior Publication Data

US 2004/0147930 A1 Jul. 29, 2004

(30) Foreign Application Priority Data

Dec. 19, 2002 (DE) ................. 202 19 683

(51) Int. Cl.
*A61B 17/56* (2006.01)
*A61B 17/58* (2006.01)
*A61F 2/30* (2006.01)

(52) U.S. Cl. ...................................... 606/64
(58) Field of Classification Search .................. 606/53, 606/60, 62, 63, 64, 65, 66; 411/535, 536, 411/544, 545
See application file for complete search history.

(56) References Cited

U.S. PATENT DOCUMENTS

| 3,942,407 | A | * | 3/1976 | Mortensen | ............... 411/36 |
|---|---|---|---|---|---|
| 4,236,512 | A | * | 12/1980 | Aginsky | ............... 606/68 |
| 4,388,921 | A | * | 6/1983 | Sutter et al. | ............... 606/71 |
| 5,032,125 | A | * | 7/1991 | Durham et al. | ............... 606/62 |
| 5,454,813 | A | * | 10/1995 | Lawes | ............... 606/62 |
| 5,578,035 | A | * | 11/1996 | Lin | ............... 606/68 |
| 6,010,505 | A | | 1/2000 | Asche et al. | |
| 6,235,031 | B1 | * | 5/2001 | Hodgeman et al. | ............... 606/64 |
| 6,337,142 | B2 | | 1/2002 | Harder et al. | |
| 6,443,954 | B1 | * | 9/2002 | Bramlet et al. | ............... 606/62 |
| 6,645,209 | B2 | * | 11/2003 | Hall et al. | ............... 606/69 |
| 6,648,889 | B2 | * | 11/2003 | Bramlet et al. | ............... 606/62 |
| 2002/0055743 | A1 | | 5/2002 | Seemann | |
| 2004/0122428 | A1 | | 6/2004 | Johnstone | |

FOREIGN PATENT DOCUMENTS

| DE | 297 19 293 U1 | | 4/1998 |
| DE | 198 52 945 A1 | | 5/2000 |
| EP | 321170 A1 | * | 6/1989 |
| EP | 0 968 685 A2 | | 1/2000 |

\* cited by examiner

*Primary Examiner*—Anu Ramana
(74) *Attorney, Agent, or Firm*—Lerner, David, Littenberg, Krumholz & Mentlik, LLP

(57) ABSTRACT

An osteosynthetic aid for tubular bones includes a locking nail which has a shank and, at the two ends of said shank, has at least one cross-bore for a headed locking screw. A biasing sleeve is resiliently deformable in an axial direction and is disposed between the head of the locking screw and the shank of the locking nail. The sleeve maintains the cross-locking screw under tension to keep the shank of the nail from shifting during use.

10 Claims, 2 Drawing Sheets

OSTEOSYNTHETIC AID

BACKGROUND OF THE INVENTION

The invention relates to an osteosynthetic aid for tubular bones. More specifically, the invention relates to a locking nail system as has become known for the fixation of fractures of tubular bones, particularly the femur, tibia or humerus. The basic principle is embodied in an elongate nail shank which has at least one cross-bore at each of its ends. The cross-bore is traversed by a bone screw or locking screw with which the nail shank is located in the bone in both the axial and rotational directions.

A peculiar problem in using locking nails of this type, e.g. for humeral head fractures, is posed by the postsurgical migration of the screws. Since the bone fragments may move or the bone is resorbed the bias which is produced while the locking nail is screwed in can be lost and, as a result, can cause the locking screw to come unscrewed.

When the locking nail is employed as a supracondylar nail it is known to pass a so-called tibial bolt through the condyles. It usually comprises a tibial bolt which has a relatively long shank and a threaded portion, and a tibial nut which is screwed onto the shank. The tibial nut can have a sleeve-shaped portion to allow a smooth shank to be formed between the nut and the head of the screw. If such a treatment is applied, also because bone elements are resorbed or fragments will shift, it might happen that it is no longer possible to sufficiently secure the location of the nail shank, i.e. it will migrate away sidewards, for example.

SUMMARY OF THE INVENTION

It is the object of the invention to provide an osteosynthetic aid which ensures that the tension originally applied to a locking screw or tibial bolt essentially is maintained even after some time.

In the invention, a biasing sleeve which resiliently gives way or deformed in an axial direction, is disposed between the head of the locking screw and the nail shank.

According to an aspect of the invention, the biasing sleeve can have a radial flange at one end against which the head of the locking screw comes to bear.

When the invention is employed, the hole which is drilled in the bone after the cross-bore is found in the nail shank has to be provided with a diameter that also allows the introduction of the sleeve. The sleeve is dimensioned so that it comes to bear against the nail shank, thereby causing its flange to bear on the outer corticalis. Now, when the locking screw is turned in and is tightened the biasing sleeve is set to an axial bias or tension. Such bias provides for the tension to be maintained even when the distance changes between the corticalis and the nail shank because of changes within the bone. At this stage, the flange constitutes an abutment for the corticalis in applying the axial bias.

It is particularly advantageous to apply the invention to nail shanks the cross-bore of which has a thread which interengages with the thread of the locking screw. Such a construction not only helps predetermine an axial and rotational position, but also locate the lateral position of the nail.

According to the invention, when applied to a supracondylar nail, a provision is made to dispose a first biasing sleeve between the head of the tibial bolt and the nail shank and to dispose a second biasing sleeve between the nail shank and tibial nut. Such a configuration prevents the bolted joint of the tibial bolt from becoming loose, on one hand, and the nail shank from moving sidewards (windshield wiper effect), on the other.

Various constructional approaches are imaginable to achieve an elastic action in an axial direction by means of a metallic sleeve. According to the invention, one approach provides that the biasing sleeve be given a series of axially spaced circumferential slots which are circumferentially offset. Preferably, the slots overlap each other circumferentially and preferably extend through an angle of more than 180°. According to another aspect of the invention, the offset between adjacent circumferential slots can be 90°, for example. It is also possible to use a coil spring for the biasing sleeve.

BRIEF DESCRIPTION OF THE DRAWINGS

The invention will be described in more detail below with reference to two embodiments.

DETAILED DESCRIPTION OF THE PREFERRED EMBODIMENTS

Figure 1:
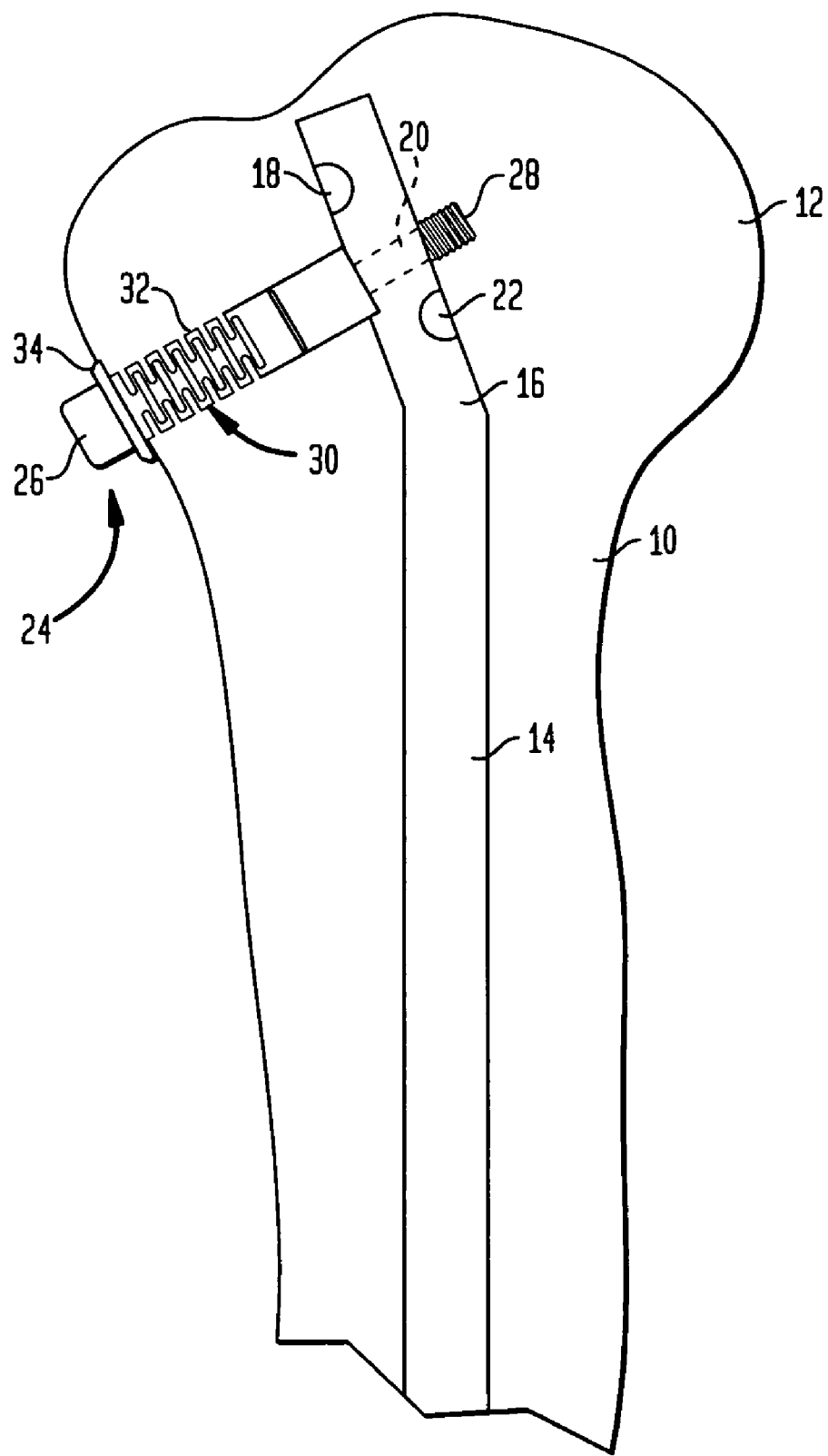
FIG. 1 schematically shows a locking nail in a humerus to provide the humeral head with a biasing sleeve of the invention.

Referring to FIG. 1, there is shown the proximal portion of a humerus generally denoted as 10. The humeral head is denoted as 12. A locking nail 14 of a conventional structure is introduced through head 12. In the preferred embodiment, it is curved or bent at 16. In the preferred embodiment, the proximal portion has three cross-bores 18, 20 and 22 which are angularly offset and are located at an axial distance from each other. Preferably, they are provided with a thread (not shown).

The cross-bores 18 to 22 serve for the reception of a locking screw one of which is shown at 24. Screw 24 has a head 26 and a shank 28 which has a threaded portion. The threaded portion is seated in the thread of cross-bore 20. Arranged on the shank 28 of locking screw 24 is a sleeve 30 which has a shank 32 positioned in an axial direction, and a radially circumferential flange 34 at one end.

During a surgery, the corticalis of the humerus 10 is bored open to such an extent that the biasing sleeve 30 can be passed through with the flange 34 coming to bear against the outer surface of the corticalis. Head 26 of locking screw 24 comes to bear on flange 34 while the locking screw is being threaded in. This is accomplished in a way that sleeve 30 is set to an axial bias, i.e. is slightly contracted in an axial direction. If the distance increases between the nail 14 and the corticalis the biasing sleeve 30 causes the locking screw to be maintained under sufficient tension and to be prevented from migrating away.

Figure 2:
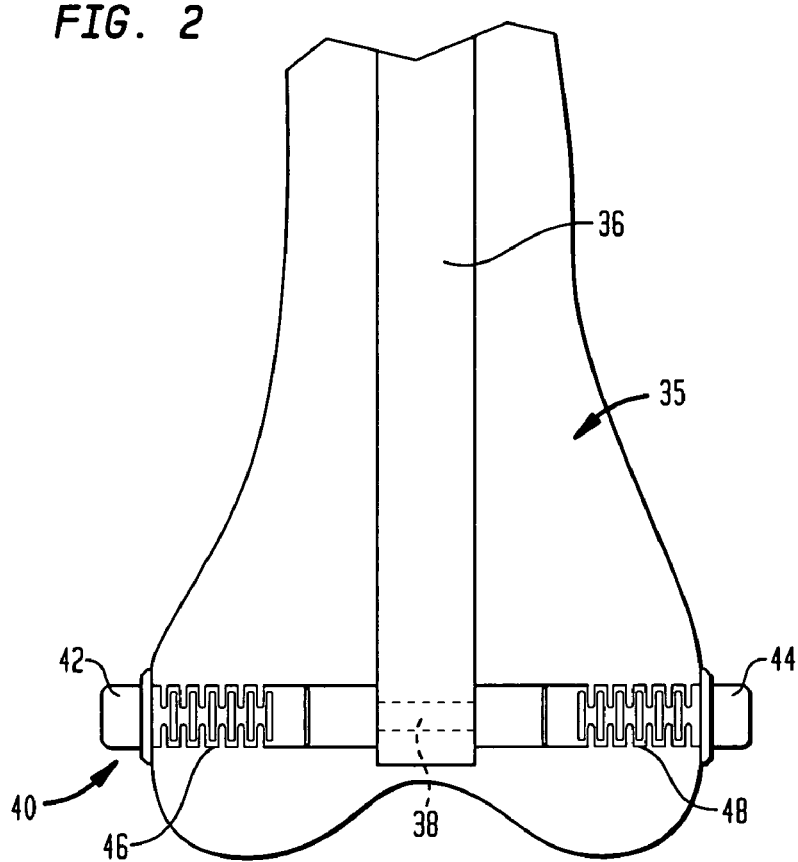
FIG. 2 schematically shows the distal femur with two biasing sleeves and a tibial bolt.

Referring to FIG. 2, a distal femur portion is outlined at 35. A locking nail 36 is driven in between the condyles from the underside, as is known and shown in U.S. Pat. No. 6,010,505 and U.S. Publication No. 20020055743. As is typical, the nail has at least one lower cross-bore in the distal area and has at least one upper cross-bore (not shown) in the proximal area. The lower cross-bore is designated 38. It is traversed by the shank of a tibial bolt 40 which cannot be seen in detail and which has a head 42. Bolt 40 is similar to that shown in U.S.

Pat. No. 6,010,505. The end of the tibial bolt 40, which protrudes on the opposite side of the respective condyle, has screwed thereon a tibial nut 44. This locates the shank of the nail 36 in both the axial and rotational directions. In the preferred embodiment, a biasing sleeve 46 and 48, respectively, is disposed between the nail shank 36 and the head 42 of the tibial bolt 40, on one hand, and between the shank and the tibial nut 44, on the other. In the preferred embodiment, its structure is the same as that of sleeve 30 of FIG. 1.

The assembly described helps in axially biasing the biasing sleeves 46, 48 which ensure that if the bolted joint becomes loose the nail shank does not shift and the bolt elements do not migrate.

Figure 3:
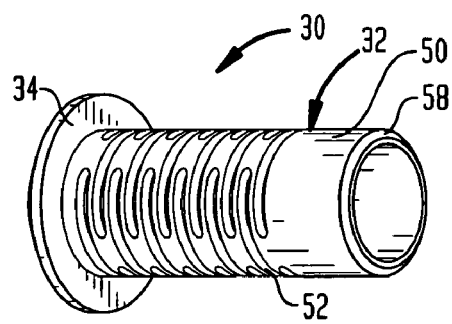
FIG. 3 shows a perspective view of a biasing sleeve of the invention.
Figure 4:
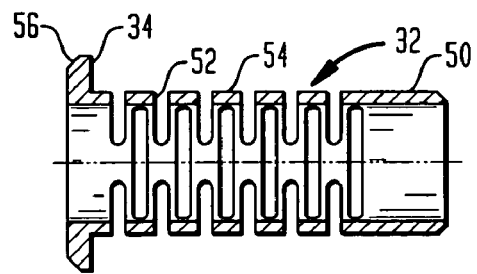
FIG. 4 shows a section through the biasing sleeve of FIG. 3.

FIGS. 3 and 4 illustrate a preferred embodiment of such a sleeve, e.g. sleeve 30. A smooth sleeve portion 50 is provided at the end opposed to flange 34. A series of axially spaced circumferential slots 52 are provided between the portion 50 and flange 34 which extend through more than 180° around the circumference of the sleeve and overlap each other by 90° each. Preferably, the width of the slots is somewhat less than the width of the web portions 54 between adjacent slots 52. This achieves a sufficient elastic action when the appropriate material is chosen and the thickness is sufficient.

As can be seen from FIG. 4, the annular flange 34 has a circumferential chamfer 56 at the edge opposed to the shank 32. At the free end, the smooth portion 50 is also provided with a chamfer 58 to facilitate introduction into the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An osteosynthetic aid for tubular bones, comprising a locking nail which has a longitudinally extending shank with first and second ends and defining an outer bone contacting surface, at least one cross-bore extending along an axis transverse to a longitudinal axis of the shank and a locking screw having a head for extending through said cross-bore and a biasing sleeve which extends adjacent the locking screw along the transverse axis and resiliently axially deforms in the direction along the transverse axis between the head of the locking screw and an outer shank surface surrounding the cross-bore in the locking nail shank wherein the sleeve has a radial flange at a first end against which the head of the locking screw comes to bear and the sleeve has a second end opposite the first end, the second end having a lower surface that bears against the outer bone contacting surface of the locking nail shank and is held axially in position by engagement with the nail shank outer surface surrounding the bore wherein the locking screw has a threaded portion which interengages with a thread of a cross-bore.

2. An osteosynthetic aid for tubular bones, comprising a locking nail which has a longitudinally extending shank with first and second ends and, has at least one cross-bore extending along an axis transverse to a longitudinal axis of the shank and a locking screw having a head for extending through said cross-bore and a biasing sleeve which extends adjacent the locking screw along the transverse axis and resiliently deforms in the direction along the transverse axis between the head of the locking screw and an outer shank surface surrounding the cross-bore in the locking nail shank wherein the locking screw is a tibial bolt which has a first head at one end and a second end onto which the tibial nut is adapted to be screwed and a first biasing sleeve is disposed between the head of the tibial bolt and the locking nail shank and a second biasing sleeve is disposed between the locking nail shank and the tibial nut.

3. An apparatus for fixing a shank of an implant for a long bone in a direction transverse to an axis of the long bone, comprising:
   a screw having a first portion including an end with a first head and a leading second portion for insertion through a bore in an implant shank, the bore extending along an axis transverse to a longitudinal axis of the implant shank;
   a first biasing element having a deformable wall surrounding a central opening for receiving the screw second portion, said first head engaging a first end of said biasing element, an outer surface of the shank surrounding the bore in said implant shank engaging a leading second end of said biasing element, the biasing element resiliently deformable along the transverse axis wherein said screw second portion is releasably coupled to said first portion, said screw second portion having an end opposite said end of said screw first portion having the screw first head, said end of the screw second portion including a second head or nut, the apparatus further including a second biasing element resiliently deformable along the transverse axis having a first end for engaging the second head or nut of the screw second portion and a second end opposite the first end of the second biasing element engaging an outer surface of the implant shank.

4. The apparatus as set forth in claim 3 wherein the biasing element is a sleeve having a series of axially spaced circumferentially extending slots which are circumferentially offset from one another.

5. The apparatus as set forth in claim 4 wherein end portions of the circumferential slots overlap one another.

6. The apparatus as set forth in claim 5 wherein the circumferential slots extend through an angle of more than 180°.

7. The apparatus as set forth in claim 6 wherein adjacent slots are offset by about 90° from one another.

8. A method for fixing an implant shank in a long bone, comprising:
   inserting a shank into the long bone, the shank having an opening therein extending along an axis transverse to an axis of a long bone,;
   aligning a biasing sleeve having deformable walls extending between first and second ends thereof, the walls surrounding a central bore therein, with the transverse opening in the shank the biasing sleeve second end engaging an outer surface of the shank surrounding the transverse opening;
   inserting a bone screw having a first portion including an end with a head and a threaded second portion through said biasing sleeve and into said transverse opening in said shank;
   compressing said biasing sleeve by deforming the walls thereof in the direction of the transverse axis by tightening said bone screw so that the head thereof engages the first end of the biasing sleeve and the second end of said sleeve engages a first side surface of said shank wherein said compressing includes inserting said threaded screw second portion into a threaded nut aligned with said transverse shank opening on a second side of said opposite said first side.

9. A method for fixing an implant shank in a long bone, the shank having an opening therein extending along an axis transverse to an axis of a long bone, comprising:
   inserting said shank into the long bone;

aligning a biasing sleeve having deformable walls extending between first and second ends thereof surrounding a central bore therein with the transverse opening in the shank;

inserting a bone screw having a first portion including an end with a head and a threaded second portion through said biasing sleeve and into said transverse opening in the shank;

compressing the biasing sleeve by deforming the walls thereof by tightening said bone screw so that the head thereof engages the first end of the biasing sleeve and the second end of said sleeve engages a first side of said shank, wherein said compressing includes inserting said threaded screw second portion into a threaded nut aligned with said transverse opening on a second side of said shank opposite said first side, further comprising inserting a second biasing sleeve between said nut and said second side of said shank and compressing said second biasing sleeve by tightening said bone screw.

10. An apparatus for fixing a shank of an implant for a long bone in a direction transverse to an axis of the long bone, comprising:

a screw having a first portion including an end with a head and a second portion for insertion through a bore in said shank;

a first biasing element having a deformable wall surrounding a central opening for receiving the screw first portion, said head of the first screw portion engaging a first end of said biasing element, wherein an implant shank portion engages a second end of said biasing element, said screw second portion is releasably coupled to said screw first portion, said screw second portion having an end opposite said end of said screw first portion, said screw second portion end including a head, and further including a second biasing element having a first end for engaging the head of the screw second portion and a second end of the second biasing element engaging an implant shank portion.

* * * * *

UNITED STATES PATENT AND TRADEMARK OFFICE
CERTIFICATE OF CORRECTION

PATENT NO. : 7,569,055 B2
APPLICATION NO. : 10/735975
DATED : August 4, 2009
INVENTOR(S) : Nils Zander et al.

Page 1 of 1

It is certified that error appears in the above-identified patent and that said Letters Patent is hereby corrected as shown below:

Column 1, line 40, "direction, is disposed" should read --direction is disposed--.
      Column 3, line 5, "embodiment, a biasing sleeve" should read --embodiment, biasing sleeves--.
      Column 3, line 6, "is disposed" should read --are disposed--.
      Column 3, line 58, "and, has" should read --and has--.
      Column 4, line 21, "said first" should read --said screw first--.
      Column 4, line 22, "having the screw" should read --having the--.
      Column 4, line 48, "shank the biasing" should read --shank, the biasing--.
      Column 4, line 62, "transverse shank opening on a second side of said" should read --transverse opening on a second side of said shank--.

Signed and Sealed this

Ninth Day of November, 2010

David J. Kappos
*Director of the United States Patent and Trademark Office*